US006284470B1

(12) United States Patent
Bitner et al.

(10) Patent No.: US 6,284,470 B1
(45) Date of Patent: Sep. 4, 2001

(54) KITS FOR CELL CONCENTRATION AND LYSATE CLEARANCE USING PARAMAGNETIC PARTICLES

(75) Inventors: Rex M. Bitner, Cedarburg; Craig E. Smith, Oregon; Douglas H. White; Braeden L. Butler, both of Madison; Jacqui Sankbeil, Edgerton, all of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/645,133

(22) Filed: Aug. 24, 2000

Related U.S. Application Data

(60) Division of application No. 09/475,958, filed on Dec. 30, 1999, and a continuation-in-part of application No. 09/064,449, filed on Apr. 22, 1998, now Pat. No. 6,194,562.
(60) Provisional application No. 60/134,156, filed on May 14, 1999.

(51) Int. Cl.$^7$ ............................ C12Q 1/68; G01N 33/551; G01N 33/552
(52) U.S. Cl. ...................... 435/6; 435/91.1; 536/23.1; 436/501; 436/526; 436/527
(58) Field of Search .................. 536/23.1; 436/526, 436/527, 501; 435/91.1, 6

(56) References Cited

U.S. PATENT DOCUMENTS

| | | |
|---|---|---|
| 3,652,761 | 3/1972 | Weetall . |
| 4,233,169 | 11/1980 | Beall et al. . |
| 4,297,337 | 10/1981 | Mansfield et al. . |
| 4,395,271 | 7/1983 | Beall et al. . |
| 4,672,040 | 6/1987 | Josephson . |
| 4,695,393 | 9/1987 | Whitehead et al. . |
| 4,699,717 | 10/1987 | Riesner et al. . |
| 4,767,670 | 8/1988 | Cox et al. . |
| 4,927,750 * | 5/1990 | Dorn ............................ 435/2 |
| 5,057,426 | 10/1991 | Henco et al. . |
| 5,075,430 | 12/1991 | Little . |
| 5,076,950 | 12/1991 | Ullman et al. . |
| 5,155,018 | 10/1992 | Gillespie et al. . |
| 5,234,809 | 8/1993 | Boom et al. . |
| 5,316,680 | 5/1994 | Frechet et al. . |
| 5,346,994 | 9/1994 | Chomczynski . |
| 5,389,449 | 2/1995 | Afeyam et al. . |
| 5,395,498 | 3/1995 | Gombinsky et al. . |
| 5,523,231 | 6/1996 | Reeve . |
| 5,582,988 | 12/1996 | Backus et al. . |
| 5,610,274 | 3/1997 | Wong et al. . |
| 5,652,348 | 7/1997 | Burton et al. . |
| 5,658,548 | 8/1997 | Padhye et al. . |
| 5,660,984 | 8/1997 | Davis et al. . |
| 5,681,946 | 10/1997 | Reeve . |
| 5,693,785 | 12/1997 | Woodward et al. . |
| 5,728,822 | 3/1998 | Macfarlane . |
| 5,734,020 | 3/1998 | Wong et al. . |
| 5,747,663 | 5/1998 | Colpan et al. . |
| 5,783,686 | 7/1998 | Gonzalez . |
| 5,789,148 * | 8/1998 | Van Vlasselaer et al. ............... 435/2 |
| 5,861,315 * | 1/1999 | Nakahata ............................. 435/384 |
| 5,898,071 | 4/1999 | Hawkins . |
| 5,904,848 | 5/1999 | Wong et al. . |
| 5,945,525 | 8/1999 | Uematsu et al. . |
| 5,990,301 | 11/1999 | Colpan et al. . |
| 6,027,945 | 2/2000 | Smith et al. . |
| 6,117,398 | 9/2000 | Bienhaus et al. . |

FOREIGN PATENT DOCUMENTS

| | | |
|---|---|---|
| 2223821 | 6/1996 | (CA) . |
| 0 741 141 A2 | 11/1996 | (EP) . |
| 0757106A2 | 2/1997 | (EP) . |
| 9327290 | 12/1997 | (JP) . |
| 9327291 | 12/1997 | (JP) . |
| WO 83/03363 | 10/1983 | (WO) . |
| WO 91/12079 | 8/1991 | (WO) . |
| WO 95/06652 | 3/1995 | (WO) . |
| WO 97/29825 | 8/1997 | (WO) . |
| WO 98/31461 | 7/1998 | (WO) . |
| WO 98/31840 | 7/1998 | (WO) . |
| 98/31840 * | 7/1998 | (WO) . |

OTHER PUBLICATIONS

Sambrook, J., et al. (1989) In *Molecular Cloning A Laboratory Manual*, 2nd edition, Cold Spring Harbor Laboratory Press, pp. 2.22 and filtration system reference.

Sambrook, J., et al. (1989) In *Molecular Cloning A Laboratory Manual*, 2nd edition, Cold Spring Harbor Laboratory Press, pp. 1.25–1.28.

*Kurt–Othmer Encyclopedia of Chemical Technology*, vol. 21, 4th ed., Mary Howe–Grant, ed., John Wiley & Sons, pub., 1997, pp. 1021–1022.

Technical Bulletin No. 202 Wizard ® *Plus* Series 9600 ™ DNA Purification System, (Promega Corp.).

Technical Bulletin No. 225 Wizard ® *Plus* SV Minipreps DNA Purification System, (Promega Corp.).

Technical Bulletin No. 259 Wizard ® PureFection Plasmid DNA Purification System, (Promega Corp.).

(List continued on next page.)

Primary Examiner—David Guzo
(74) Attorney, Agent, or Firm—Grady J. Frenchick; Karen B. King; Michael Best & Friedrich LLP

(57) ABSTRACT

Methods are disclosed for using paramagnetic particles to concentrate or harvest cells. Methods are also disclosed for clearing a solution of disrupted biological material, such as a lysate of cells or a homogenate of mammalian tissue. Methods are also disclosed for using paramagnetic particles to isolate target nucleic acids, such as RNA or DNA, from a solution cleared of disrupted biological material using the same type or a different type of paramagnetic particle. Kits are also disclosed for use with the various methods of the present invention. Nucleic acids isolated according to the present methods and using the present kits are suitable for immediate use in downstream processing, without further purification.

5 Claims, 3 Drawing Sheets

OTHER PUBLICATIONS

Anspach, "High–Performance Liquid Affinity Chromatography with Phenylboronic Acid, Benzamidine, Tri–L–alanine, and Concanavalin A Immobilized on 3–Isothiocyanatopropytriethoxysilane–Activated Nonporous Monodisperse Silicas", *Anal. Biochem* (1989) 179:171–181.

Ansubel et al., *Current Protocols in Molecular Biology*, Ch. 2 (DNA), Ch. 4 (RNA).

Bishoff et al., "Chemically Synthesized Hydrophobic Anion–Exchange High–Performance Liquid Chromatography Supports Used for Oligonucleotide Resolution By Mixed Mode Chromatography", *J. Chromatog.* (1983) 270:117–126.

Bishoff et al., "Nucleic Acid Resolution By Mixed–Mode Chromatography", *J. Chromatog.* (1984) 296:329–337.

Boom et al., "Rapid and Simple Method for Purification of Nucleic Acids", *J. Clin. Mircrobiol.*, (1990) 28:495–503.

Crowother et al.. "High–Performance Liquid Chromatographic Separation of Oligonucleotides and Other Nucleic Acid Constitutents on Multifunctional Stationary Phases", *J. Chromatog.* (1983) 282:619–628.

Edwardson et al.. "Separation and purification of oligonucleotides using a new bonded–phase packing material", *J.Chromatog.* (1991) 545:79–89.

Figueroa et al, "High–Performance Immobilized–Metal Affinity Chromatography of Proteins on Iminodiacetic Acid Silica–Based Bonded Phases", *J. Chromatog.* (1986) 371:335–352.

Floyd et al., "Mixed–Mode Hydrophobic Ion Exchange for the Separation of Oligonucleotides and DNA Fragments Using HPLC", *Analytical Biochemistry* (1986) 154:570–577.

Gjerd et al., Ion Chromatography, Ch. 3, Dr. Alfred Hothig Verlag Heidelberg (1987) 2nd Ed.

Goldsborough et al., "High Purity Plasmid DNA from Anion Exchange Chromatography", *Focus* (1998) vol. 20 No. 3.

Jose et al., "Application of a Weakly Basic Dimethylamino–Modified Silica Ion Exchanger to the Separation of oligonucleotides", *J. Chromatog.* 185 (1979) 403–412.

Kirk–Othmer, Encyclopedia of Chemical Technology, (1993) vol. 6, 4th ed., pp. 773–775.

Kleiber et al., Database CAS online AN 126:86772 9 pp. Abstract.

Maa et al., "Rapid high–performance liquid chromatography of nucleic acids with polystyrene–based micropellicular anion exchangers", *J. Chromatog.* (1990) 508:61–73.

Macherey–Nagel, Macherey–Nagel homepage on the Internet on Jun. 12, 1998, at http://www.machrey–nagel.com.

Marko et al., "A Procedure for the Large–Scale Isolation of Highly Purified Plasmid DNA Using Alkaline Extraction and Binding to Glass Powder", *Anal. Biochem.* (1982)121:382–387.

McLaughlin, L., "Mixed–Mode Chromatography of Nucleic Acids", *Chem Rev* (1989) 89: 309–319.

Northrop, et al., "Preparation and Evaluation of a Bimodal Size–Exclusion Chromatography Column Containing a Mixture of Two Silicas of Different Pore Diameter", *Anal. Chem.* (1991) 63:1350–1354.

QuantiBlot, QuantiBlot Human DNA Quantitation System, PE Applied Biosystems, Feb. 5, 1996, p. 1–5.

Uematsu et al., Databas CAS online AN 126:182277 9 pp. Abstract (EP 0 757 106 A2).

Vogelstein et al., "Preparative and Analytical Purification of DNA from Agarose", *Proc. Natl. Acad. Sci.* (1979) vol. 76, No. 2:615–619.

Waterborg et al., "Efficient large–scale purification of restriction fragments by solute–displacement ion–exchange HPLC", *Nucleic Acids Research* (1993) vol. 21, No. 12:2913–2915.

* cited by examiner

MagIE-glycidyl-histidine | Magnasil™
1mg  2mg  4mg | 4mg

Spin   Mag   Spin   Mag   Spin   Mag
1ml    1ml   2ml    2ml   3ml    3ml

KITS FOR CELL CONCENTRATION AND LYSATE CLEARANCE USING PARAMAGNETIC PARTICLES

CROSS-REFERENCE TO RELATED APPLICATIONS

This application is a divisional of U.S. application Ser. No. 09/475,958, filed Dec. 30, 1999, which claims the benefit of U.S. Provisional Application No. 60/134,156, filed May 14, 1999. This application is also a continuation-in-part of U.S. application Ser. No. 09/064,449, filed Apr. 22, 1998, now U.S. Pat. No. 6,194,562.

STATEMENT REGARDING FEDERALLY SPONSORED RESEARCH OR DEVELOPMENT

Not applicable.

TECHNICAL FIELD

This invention relates generally to the use of magnetically responsive particles, such as magnetically responsive silica gel particles or magnetically responsive ion exchange particles, to harvest or to concentrate cells or biological tissue. This invention also relates to the use of such particles to clear lysates or homogenates of such cells or tissue. This invention relates, furthermore, to the use of such particles to isolate target nucleic acids, such as plasmid DNA, chromosomal DNA, DNA fragments, total RNA, mRNA, or RNA/DNA hybrids from non-target material in a cell lysate.

BACKGROUND OF THE INVENTION

Cells in a liquid culture must be concentrated or harvested before they can be preserved for later use, stained for direct analysis, or processed to isolate target specific materials therefrom. Most cell harvesting and concentration techniques involve centrifugation, filtration, or a combination of centrifugation and filtration. (See, e.g. *Molecular Cloning*, (1989) ed. by Sambrook et al., pp 2.22 and filtration system reference). Unfortunately, neither filtration nor centrifugation is amenable to automation. Specifically, neither can be performed at basic pipettor-diluter robotics stations, such as the Biomec®. When it becomes necessary to isolate or analyze certain types of material in the interior of a cell, such as a target nucleic acid or a protein, the cell membrane must be disrupted and the contents of the cell released into the solution surrounding the cell. Such disruption can be accomplished by mechanical means (e.g., by sonication or by blending in a mixer), by enzymatic digestion (e.g. by digestion with proteases), or by chemical means (e.g., by alkaline lysis followed by addition of a neutralization solution). Whatever means is used to disrupt a cell, the end product, referred to herein as a lysate solution, consists of the target material and many contaminants, including cell debris. The lysate solution must be cleared of as many of the large contaminants as possible before the target material can be further isolated therefrom. Either or both of the same two means described above, i.e. centrifugation and filtration, have been used to clear lysate solutions prior to further processing. However, for reasons given above, neither means of clearing a lysate solution is amenable to automation.

Many different systems of materials and methods have been developed for use in the isolation of nucleic acids from cleared lysate solutions. Many such systems are silica based, such as those which employ controlled pore glass, filters embedded with silica particles, silica gel particles, resins comprising silica in the form of diatomaceous earth, glass fibers or mixtures of the above. Each such silica-based solid phase separation system is configured to reversibly bind nucleic acid materials when placed in contact with a medium containing such materials in the presence of chaotropic agents. The silica-based solid phases are designed to remain bound to the nucleic acid material while the solid phase is exposed to an external force such as centrifugation or vacuum filtration to separate the matrix and nucleic acid material bound thereto from the remaining media components. The nucleic acid material is then eluted fiom the solid phase by exposing the solid phase to an elution solution, such as water or an elution buffer. Numerous commercial sources offer silica-based resins designed for use in centrifugation and/or filtration isolation systems, e.g. Wizard® DNA purification systems products from Promega Corporation (Madison, Wis., U.S.A.), or the QiaPrep® DNA isolation systems from Qiagen Corp. (Chatsworth, Calif., U.S.A.). Unfortunately, the type of silica-based solid phases described above all require one use centrifugation or filtration to perform the various isolation steps in each method, limiting the utility of such solid phases in automated systems.

Magnetically responsive solid phases, such as paramagnetic or superparamagnetic particles, offer an advantage not offered by any of the silica-based solid phases described above. Such particles could be separated from a solution by turning on and off a magnetic force field, or by moving a container on to and off of a magnetic separator. Such activities would be readily adaptable to automation.

Magnetically responsive particles have been developed for use in the isolation of nucleic acids. Such particles generally fall into either of two categories, those designed to reversibly bind nucleic acid materials directly, and those designed to reversibly bind nucleic acid materials through an intermediary. For an example of particles of the first type, see silica based porous particles designed to reversibly bind directly to DNA, such as MagneSil™ particles from Promega, or BioMag® magnetic particles from PerSeptive Biosystems. For examples of particles and systems of the second type designed to reversibly bind one particular type of nucleic acid (mRNA), see the PolyATract® Series 9600™ mRNA Isolation System from Promega Corporation (Madison, Wis., U.S.A.); or the streptavidin coated microsphere particles from Bangs Laboratories (Carmel, Ind., U.S.A.). Both of these systems employ magnetically responsive particles with streptavidin subunits covalently attached thereto, and biotin with an oligo(dT) moiety covalently attached thereto. The biotin-oligo(dT) molecules act as intermediaries, hybridizing to the poly(A) tail of mRNA molecules when placed into contact therewith, then binding to the streptavidin on the particles. The mRNA molecules are then released in water.

Indirect binding magnetic separation systems for nucleic acid isolation or separation require at least three components, i.e. magnetic particles, an intermediary, and a medium containing the nucleic acid material of interest. The intermediary/nucleic acid hybridization reaction and intermediary/particle binding reaction often require different solution and/or temperature reaction conditions from one another. Each additional component or solution used in the nucleic acid isolation procedure adds to the risk of contamination of the isolated end product by nucleases, metals, and other deleterious substances.

Various types of magnetically responsive silica based particles have been developed for use as solid phases in direct or indirect nucleic acid binding isolation methods.

One such particle type is a magnetically responsive glass bead, preferably of a controlled pore size. See, e.g. Magnetic Porous Glass (MPG) particles from CPG, Inc. Lincoln Park, N.J., U.S.A.); or porous magnetic glass particles described in U.S. Pat. Nos. 4,395,271; 4,233,169; or 4,297,337. Nucleic acid material tends to bind very tightly to glass, however, so that it can be difficult to remove once bound thereto. Therefore, elution efficiencies from magnetic glass particles tend to be low compared to elution efficiencies from particles containing lower amounts of a nucleic acid binding material such as silica.

Another type of magnetically responsive particle designed for use as a solid phase in direct binding and isolation of nucleic acids, particularly DNA, is a particle comprised of agarose embedded with smaller ferromagnetic particles and coated with glass, e.g. U.S. Pat. No. 5,395,498. Yet another type of magnetically responsive particle designed for direct binding and isolation of nucleic acids is produced by incorporating magnetic materials into the matrix of polymeric silicon dioxide compounds, e.g. German Patent Application No. DE 43 07 262. The latter two types of magnetic particles, the agarose particle and the polymeric silicon dioxide matrix, tend to leach iron into a medium under the conditions required to bind nucleic acid materials directly to each such magnetic particle. It is also difficult to produce such particles with a sufficiently uniform and concentrated magnetic capacity to ensure rapid and efficient isolation of nucleic acid materials bound thereto.

Magnetically responsive beads designed for use in the isolation of target polymers, such as nucleic acids, and methods for their use therein are described in U.S. Pat. No. 5,681,946 and in International Publication No. WO 91/12079. These last beads are designed to become nonspecifically associated with the target polymer, only after the target polymer is precipitated out of a solution comprising the target polymer and the beads. Magnetic force is used to isolate the beads and polymer associated therewith from the solution. The magnetically responsive beads recommended for use in this last system are "finely divided magnetizable material encapsulated in organic polymer." ('946 Patent, col. 2, line 53).

A variety of solid phases have also been developed with ion exchange ligands capable of exchanging with nucleic acids. However, such systems are generally designed for use as a solid phase of a liquid chromatography system, for use in a filtration system, or for use with centrifugation to separate the solid phase from various solutions. Such systems range in complexity from a single species of ligand covalently attached to the surface of a filter, as in DEAE modified filters (e.g., CONCERT® isolation system, Life Technology Inc., Gaithersburg, Md., U.S.A.), to a column containing two different solid phases separated by a porous divider (e.g., U.S. Pat. No. 5,660,984), to a chromatography resin with pH dependent ionizable ligands covalently attached thereto (e.g., U.S. Pat. No. 5,652,348).

Materials and methods are needed which enable one to automate as many steps as possible to quickly and efficiently isolate target nucleic acids from cells or mammalian tissue. Specifically, methods and materials are needed for the concentration or harvesting of cells, for the clearing of solutions of disrupted cells or tissue, and for the isolation of target nucleic acids from such cleared solutions, wherein labor-intensive steps such as filtration or centrifugation are not required. The present invention addresses each of these needs. Nucleic acids isolated according to the present method can be used in a variety of applications, including restriction digestion and sequencing.

BRIEF SUMMARY OF THE INVENTION

In the methods of the present invention, magnetic particles are used to process biological material. In one embodiment, the present invention is a method of concentrating or harvesting cells comprising the steps of (a) combining a solution with cells contained therein, such as an overnight culture of bacteria in a growth medium or white cells in whole blood with magnetic particles under conditions wherein the cells form a complex with the magnetic particles; and (b) isolating the magnetic particle/cell complex from the solution by application of magnetic force, e.g., by means of a magnet.

In another embodiment, the present invention is a method of clearing disrupted biological material, such as a cell lysate or a homogenate of mammalian tissue, comprising the steps of: (a) providing a solution comprising a disrupted biological material, such as a cell lysate or homogenized tissue; (b) combining the solution with magnetic particles under conditions wherein the disrupted biological material forms a complex with the magnetic particles; and (c) isolating the complex from the solution by application of magnetic force.

In yet another embodiment, the present invention is a method of isolating a target nucleic acid from a solution of disrupted biological material, comprising the target nucleic acid, a first non-target material, and a second non-target material, comprising the steps of: (a) combining a solution of the disrupted biological material with first magnetic particles under conditions wherein the first non-target material forms a first complex with the first magnetic particles; (b) separating the first complex from the solution of disrupted biological material by application of magnetic force, forming a cleared solution comprising the target nucleic acid and the second non-target material; (c) combining the cleared solution with second magnetic particles under conditions wherein the target nucleic acid adsorbs to the second magnetic particles, forming a second complex; (d) isolating the second complex from the cleared solution; (e) washing the second complex by combining the second complex with a wash solution and separating the second complex from the wash solution by magnetic force; and (f) combining the washed second complex with an elution solution, under conditions wherein the target material is desorbed from the second magnetic particles.

In yet another embodiment, the present invention also consists of kits with at least one type of magnetic particle and at least one solution needed to practice one or more of the methods of the invention, described above. In one such embodiment, the present invention is a kit comprising: (a) a first container of first magnetic particles with the capacity to form a first complex with first non-target material in a first solution of disrupted biological material comprising the first non-target material and the target nucleic acid; and (b) a second container of second magnetic particles with the capacity to form a second complex with the target nucleic acid, under solution conditions designed to promote the specific adsorption of the target nucleic acid to the second magnetic particles.

The methods and materials of the present invention can be used to isolate target nucleic acids including, but not limited to plasmid DNA, total RNA, mRNA, RNA/DNA hybrids, amplified nucleic acids, and genomic DNA from a variety of contaminants, including but not limited to agarose and components of a bacteria, animal tissue, blood cells, and non-target nucleic acids. Applications of the methods and compositions of the present invention to isolate nucleic acids from a variety of different media will become apparent from the detailed description of the invention below. Those skilled in the art of this invention will appreciate that the detailed description of the invention is meant to be exemplary only and should not be viewed as limiting the scope of the invention.

DETAILED DESCRIPTION OF THE INVENTION

Figure 1:
FIG. 1 is a photograph of samples of plasmid DNA isolated with MagneSil™ particles (Promega) or varying amounts of MagIE-glycidyl-histidine particles, fractionated by gel electrophoresis and visualized by staining with ethidium bromide, as described in Example 6.

The present invention will now be described in detail, in part, by reference to the following definitions.

The term "solid phase" is used herein in a standard chromatographic sense, to refer to an insoluble, usually rigid, matrix or stationary phase which interacts with a solute, in this case a tissue or cell or target nucleic acid, in a solute mixture. In the methods and kits of the present invention magnetic particles function as a solid phase when added to various solute mixtures.

The term "surface", as used herein, refers to the portion of the support material of a solid phase which comes into direct contact with a solution when the solid phase is combined therewith.

The term "silica gel" as used herein refers to chromatography grade silica gel, a substance which is commercially available from a number of different sources. Silica gel is most commonly prepared by acidifying a solution containing silicate, e.g. by acidifying sodium silicate to a pH of less than 11, and then allowing the acidified solution to gel. See, e.g. silica preparation discussion in *Kurt-Othmer Encyclopedia of Chemical Technology*, Vol. 21, 4th ed., Mary Howe-Grant, ed., John Wiley & Sons, pub., 1997, p. 1021.

As used herein, the term "silica magnetic particles" refers to silica based solid phases which are further comprised of materials which have no magnetic field but which form a magnetic dipole when exposed to a magnetic field, i.e., materials capable of being magnetized in the presence of a magnetic field but which are not themselves magnetic in the absence of such a field.

The term "magnetic", as used herein refers to temporarily magnetic materials, such as fenimagnetic or ferromagnetic materials. The term encompasses paramagnetic and superparamagnetic materials.

The term "magnetic particle" refers to a matrix comprising a core of paramagnetic or superparamagnetc materials and a solid phase capable of forming a complex with a solute of interest.

The term "silica magnetic particles", as used herein refers to paramagnetic particles comprising a superparamagnetic core coated with siliceous oxide, having a hydrous siliceous oxide adsorptive surface (i.e. a surface characterized by the presence of silanol groups).

The term "magnetic ion exchange particles", as used herein, refers to paramagnetic particles with ion exchange ligands covalently attached thereto.

The term "pH dependent ion exchange magnetic particles", as used herein, refers to magnetic particles with a plurality of ion exchange ligands covalently attached thereto, which can act as cation exchangers at one pH and as anion exchangers at another pH. Such magnetic particles are particularly well suited for use in the methods and kits of the present invention, as their binding capacity to different substrates can be adjusted merely by varying the pH or salt conditions in a solution.

The term "pH dependent ion exchange silica magnetic particles", as used herein, refers to silica magnetic particles with a plurality of ion exchange ligands covalently attached thereto, which can act as cation exchangers at one pH and as anion exchangers at another pH. Such magnetic particles are particularly well suited for use in the methods and kits of the present invention, because substrates can selectively adsorb to the hydrous siliceous oxide adsorptive surface of the particle through hydrophobic interactions, to the ion exchange ligands through ion exchange, or to both the surface and ion exchange ligands, depending upon solution conditions.

The term "nucleic acid" as used herein refers to any DNA or RNA molecule or a DNA/RNA hybrid molecule. The term includes plasmid DNA, amplified DNA or RNA fragments, total RNA, mRNA, genomic DNA, and chromosomal DNA.

The term "target nucleic acid" as used herein refers to any particular species of nucleic acid to be isolated using magnetic particles according to a method of the present invention. The target nucleic acid is preferably at least 20 nucleotides long, more preferably at least 100 nucleotides long, and most preferably at least 1,000 nucleotides long.

The methods and kits of the present invention can be used to harvest or concentrate cells, to clear a solution of disrupted biological material, and/or to isolate a target nucleic acid from a solution, preferably from a solution of cleared disrupted biological material. In at least one step of each such method, a complex is formed in a solution between a solute and magnetic particles. The resulting complex is then isolated from or removed from the solution by the application of magnetic force. Magnetic particles suitable for use in any given step of the methods and kits of the present invention have the capacity to form a complex with the solute of interest in that particular step of the method.

The solute is the type of material to be isolated from or removed from a solution, using magnetic particles, according to a method of the present invention. Cells to be concentrated or harvested are the solute in the harvesting method of the present invention. Disrupted biological material is the solute in the lysate or homogenate clearing method of the invention. A target nucleic acid is the solute when magnetic particles are used to isolate the target nucleic acid from any solution comprising the target nucleic acid and other material, such as a cleared lysate or homogenate solution.

In one aspect of the methods of the present invention, cells are harvested or concentrated using magnetic particles which can form a complex with the cells, under solution conditions designed to promote the formation of the complex. Silica magnetic particles and pH dependent ion exchange magnetic particles are both suitable for use in harvesting or concentrating cells according to the method of the present invention. However, one of ordinary skill in the art could readily select other suitable magnetic particles for use in this particular embodiment of the invention.

Conditions which promote the formation of a magnetic particle/solute complex vary, depending upon the nature of the solute and on the characteristics of the solid phase component of the magnetic particle. For example, when the magnetic particles are ion exchange magnetic particles or pH dependent ion exchange particles, the complex is preferably formed as a result of ion exchange between the solute and ion exchange ligands at the surface of the particles. In order to promote such ion exchange interaction, there must be at least some salt present in the solution to promote ion exchange with the solute, and the pH of the solution must be within the range wherein the ion exchange ligand has a charge appropriate to exchange with the solute. When the magnetic particles are silica magnetic particles, the complex is preferably formed as a result of hydrophobic interactions between the solute and particles. When the magnetic particles are pH dependent ion exchange silica magnetic particles, the complex can be formed as a result of hydrophobic interactions between the solute and the siliceous oxide surface of the particles, as a result of ion exchange between the solute and the ion exchange ligands, or as a result of a combination of the two types of interactions. Preferred salt, pH, and other solution conditions to be used to promote formation of a complex with any given preferred substrate isolated according to the present methods or using the present kits are described below.

When the solute is intact cells, the complex is preferably formed in the presence of a low molecular weight alcohol, such as ethanol or isopropanol.

When the solute is disrupted biological material, such as one finds in a cell lysate or tissue homogenate, and the magnetic particles are silica-based particles, the magnetic particle/solute complex is preferably formed in a solution which does not contain any more than trace amounts of alcohol or of chaotropic salts. Both alcohol and chaotropic salts, such as guanidine thiocyanate or guanidine isothiocyanate, promote adsorption of nucleic acid materials to such particles. It is contemplated, however, that one could practice the present method of cell lysate clearance in the presence of alcohol or chaotropic salts if the concentration of magnetic particles in a homogenate or lysate solution were low enough to clear the solution, but not high enough to adhere to a significant amount of the target nucleic acid in the solution.

When the solute is a target nucleic acid, formation of the complex is preferably done in the presence of at least one agent known to promote reversible adsorption of the target nucleic acid to the magnetic particles. The reversible adsorption reaction is preferably done through specific adsorption between the target nucleic acid and magnetic particles, leaving non-target material in solution. For example, when the target nucleic acid is plasmid DNA being isolated from a cleared lysate solution, the plasmid DNA is combined with magnetic particles under conditions wherein the plasmid DNA forms a complex therewith while non-target materials, such as proteins, lipids, and chromosomal DNA remain in solution. When the magnetic particle is an ion exchange magnetic particle, the complex is formed in the presence of a counterion and in a solution with a pH at which the ion exchange ligands have the capacity to exchange with the target nucleic acid. When the magnetic particles are silica magnetic particles, formation of the complex is preferably done in the presence of an agent selected from the group consisting of a low molecular weight alcohol, a high concentration of a non-chaotropic salt, and a chaotropic salt, or a combination of any of the above. For methods of adsorption and desorption of target nucleic acids to silica magnetic particles, which are suitable for use in the present invention, see international patent application number PCT/US98/01149 for METHODS OF ISOLATING BIOLOGICAL TARGET MATERIALS USING SILICA MAGNETIC PARTICLES, published as WO 98/31840, incorporated by reference herein.

The solid phase of the magnetic particles used in the present methods can be made of any common support material, including soft gel supports such as agarose, polyacrylamide, or cellulose, or hard support material such as polystyrene, latex, methacrylate, or silica.

When the solid phase support material is silica, it is preferably in the form of silica gel, siliceous oxide, solid silica such as glass or diatomaceous earth, or a mixture of two or more of the above. Silica based solid phases suitable for use in the pH dependent ion exchange matrixes of the present invention include the mixture of silica gel and glass described in U.S. Pat. No. 5,658,548, the silica magnetic particles described in PCT Publication Number WO 98/31840, and solid phases sold by Promega Corporation for use in plasmid DNA isolation, i.e. Wizard® Minipreps DNA Purification Resin. Silica gel particles are particularly preferred for use as the solid phase in the pH dependent ion exchange matrix and methods of the present invention. Silica gel particles are stable at much higher pressures than solid phases made from soft gel support material, making the silica gel solid phases suitable for HPLC as well as LC and batch separation applications.

Silica magnetic particles can be used to concentrate cells, clear lysates, or isolate target nucleic acids according to the methods the present invention. When silica magnetic particles are employed, the silica-based surface material of the particle specifically interacts with the various solutes isolated or removed therewith.

When the silica magnetic particles have ion exchange ligands covalently attached thereto, the silica-based surface material acts primarily as a solid support for the ion exchange ligands, which enable the particles to form complexes with the various solutes to be isolated or removed from any given solution. When used to isolate a target nucleic acid, the ion exchange ligands are preferably capable of forming a complex with the target nucleic acid by exchanging therewith at one pH, and of releasing the target nucleic acid at another pH. The most preferred ion exchange ligands are ones which complex with the target nucleic acid at a pH which is lower than a neutral pH, and which release the target nucleic acid at about a neutral pH and in low salt conditions, so the target nucleic acid released therein can used immediately, without concentration or further isolation. Such preferred ion exchange ligands and pH dependent ion exchange matricies which incorporate such ligands are described in U.S. patent application Ser. No. 09/312,172, for an invention titled pH DEPENDENT ION EXCHANGE MATRIX AND METHOD OF USE IN THE ISOLATION OF NUCLEIC ACIDS, incorporated by reference herein, an application filed concurrently with the provisional patent application on which the present non-provisional patent application is based.

When the solid support component of the pH dependent ion exchange matrix is a silica magnetic particle, the size of the particle is preferably selected as follows. Smaller silica magnetic particles provide more surface area (on a per weight unit basis) for covalent attachment to the plurality of ion exchange ligands, but smaller particles are limited in the amount of magnetic material which can be incorporated into such particles compared to larger particles. The median particle size of the silica magnetic particles used in a particularly preferred embodiment of the present invention is about 1 to 15 $\mu$m, more preferably about 3 to 10 $\mu$m, and most preferably about 4 to 7 $\mu$m. The particle size distribution may also be varied. However, a relatively narrow monodal particle size distribution is preferred. The monodal particle size distribution is preferably such that about 80% by weight of the particles are within a 10 $\mu$m range of the median particle size, more preferably within an 8 $\mu$m range, and most preferably within a 6 $\mu$m range.

The magnetic particles of the present invention can be porous or non-porous. When the magnetic particles are porous, the pores are preferably of a controlled size range sufficiently large to admit the target nucleic acid material into the interior of the solid phase particle, and to bind to functional groups or silica on the interior surface of the pores. When the magnetic particles are porous silica magnetic particles, the total pore volume of each silica magnetic particle, as measured by nitrogen BET method, is preferably at least about 0.2 ml/g of particle mass. The total pore volume of porous silica magnetic particles particularly preferred for use as components of the pH dependent ion exchange matrix of the present invention, as measured by nitrogen BET, is preferably at least about 50% of the pore volume is contained in pores having a diameter of 600 Å or greater.

Silica magnetic particles may contain substances, such as transition metals or volatile organics, which could adversely affect the utility of target nucleic acids substantially contaminated with such substances. Specifically, such contaminants could affect downstream processing, analysis, and/or use of the such materials, for example, by inhibiting enzyme activity or nicking or degrading the target nucleic acids isolated therewith. Any such substances present in the silica magnetic particles used in the present invention are preferably present in a form which does not readily leach out of the particle and into the isolated biological target material produced according to the methods of the present invention. Iron is one such undesirable at least one contaminant, particularly when the biological target material is a target nucleic acid.

Iron, in the form of magnetite, is present at the core of particularly preferred forms of silica magnetic particles used as the solid phase component of the pH dependent ion exchange matrixes of the present invention. Iron has a broad absorption peak between 260 and 270 nanometers (nm). Target nucleic acids have a peak absorption at about 260 nm, so iron contamination in a target nucleic acid sample can adversely affect the accuracy of the results of quantitative spectrophotometric analysis of such samples. Any iron containing silica magnetic particles used to isolate target nucleic acids using the present invention preferably do not produce isolated target nucleic acid material sufficiently contaminated with iron for the iron to interfere with spectrophotometric analysis of the material at or around 260 nm.

The most preferred silica magnetic particles used in the matrixes and methods of the present invention, siliceous oxide coated silica magnetic particles, leach no more than 50 ppm, more preferably no more than 10 ppm, and most preferably no more than 5 ppm of transition metals when assayed as follows. Specifically, the particles are assayed as follows: 0.33 g of the particles (oven dried at 110° C.) are combined with 20 ml. of 1N HCl aqueous solution (using deionized water). The resulting mixture is then agitated only to disperse the particles. After about 15 minutes total contact time, a portion of the liquid from the mixture is then analyzed for metals content. Any conventional elemental analysis technique may be employed to quantify the amount of transition metal in the resulting liquid, but inductively coupled plasma spectroscopy (ICP) is preferred.

At least two commercial silica magnetic particles are particularly preferred for use in the present invention, BioMag® Magnetic Particles from PerSeptive Biosystems, and the MagneSil™ Particles available from Promega Corporation (Madison, Wis.). Any source of magnetic force sufficiently strong to separate the silica magnetic particles from a solution would be suitable for use in the nucleic acid isolation methods of the present invention. However, the magnetic force is preferably provided in the form of a magnetic separation stand, such as one of the Magne-Sphere® Technology Magnetic Separation Stands (cat. nos. Z5331 to 3, or Z5341 to 3) from Promega Corporation.

When magnetic particles are used to both clear a solution of disrupted biological material and to isolate a target nucleic acid therefrom, one can use the same type of particles or a different type of particles for clearing and isolation. For purposes of this disclosure, and to emphasize the flexibility in the invention, the particles used to clear the solution of disrupted biological material are referred to as first magnetic particles, while the particles used to isolate the target nucleic acid are referred to as second magnetic particles.

When the target nucleic acid is plasmid DNA, the second magnetic particles can be added directly to cleared lysate of bacteria transfonned with the plasmid DNA, wherein the lysate is formed by alkaline lysis followed by clearance using first magnetic particles as described above. Alkaline lysis procedures suitable for use in the present invention can be found in Sambrook et al, *Molecular Cloning*, Vol.1, 2$^{nd}$ ed. (pub. 1989 by Cold Spring Harbor Laboratory Press), pp. 1.25–1.28, and in Technical Bulletin Nos. 202, 225, and 259 (Promega Corp.). When the second silica magnetic particle is a pH dependent ion exchange particle, plasmid DNA from a lysate solution prepared as described above will form a complex with the pH dependent ion exchange particles upon combination therewith, provided the overall charge of the matrix is positive, and provided the charge density is sufficiently high to enable to plasmid DNA to participate in anion exchange with the ion exchange ligands of the matrix at a first pH. Once adsorbed to the matrix to form a complex, the complex can be washed in a wash solution with buffer and salt solution conditions designed to ensure the plasmid DNA remains adsorbed to the matrix throughout any such washing steps, while removing at least one contaminant Finally, the plasmid DNA is eluted from the complex by combining the complex with an elution buffer having a second pH above that of the lysate and wash solutions, wherein the second pH is sufficiently high to promote desorption of the plasmid DNA from the matrix.

The materials and methods of the present invention can be used to isolate genomic DNA from living tissue, including but not limited to blood, semen, vaginal cells, hair, buccal tissue, saliva, tissue culture cells, plant cells, placental cells, or fetal cells present in amniotic fluid and mixtures of body fluids. When the target nucleic acid is genomic DNA, it is necessary to disrupt the tissue to release the target genomic DNA from association with other material in the tissue, so the target genomic DNA can adhere to the pH dependent ion exchange matrix in the presence of a solution at the first pH. The resulting complex of matrix and genomic DNA is separated from the disrupted tissue, and washed to remove additional contaminants (if necessary). The genomic DNA is then eluted from the complex by combining the complex with an elution solution having a second pH which is higher than the first pH.

The following, non-limiting examples teach various embodiments of the invention. In the examples, and elsewhere in the specification and claims, volumes and concentrations are at room temperature unless specified otherwise. The magnetic silica particles used in the examples below were all either porous or nonporous MagneSil™ particles having the general preferred dimensions and siliceous oxide coating described as preferred above. More specifically, the porous MagneSil™ Particles used in the Examples below were taken from either of two batches of particles having the following characteristics: (1) a surface area of 55 $m^2/g$, pore volume of 0.181 ml/g for particles of <600 Å diameter, pore volume of 0.163 ml/g for particles of >600 Å diameter, median particle size of 5.31 μm, and iron leach of 2.8 ppm when assayed as described herein above using ICP; or (2) a surface area of 49 $m^2/g$, pore volume of 0.160 ml/g (<600 Å diameter), pore volume of 0.163 ml/g (>600 Å diameter), median particle size of 5.5 Åm, and iron leach of 2.0 ppm.

One skilled in the art of the present invention will be able to use the teachings of the present disclosure to select and use magnetic particles other than the silica-based magnetic particles and ion exchange magnetic particles used to illustrate the methods and kits of the invention in the Examples, below.

The Examples should not be construed as limiting the scope of the present invention. Other magnetic silica particles and their use in the present method to concentrate cells, to clear solutions of disrupted biological material, and to isolate target nucleic acids from disrupted biological material will be apparent to those skilled in the art of chromatographic separations and molecular biology.

EXAMPLES

The following examples are given to illustrate various aspects of the invention, without limiting the scope thereof:

Example 1

Gel Electrophoresis

Samples of target nucleic acids isolated according to procedures described in Examples below were analyzed for contamination with non-target nucleic acids, and for size as follows. The samples were fractionated on an agarose gel of appropriate density (e.g., a 1.0% agarose gel was used to analyze plasmid DNA, while a 1.5% agarose gel was used to analyze RNA). The fractionated nucleic acid was visualized using a fluorescent label or by dying the gel with a DNA sensitive stain, such as ethidium bromide or silver staining. The resulting fractionated, visualized nucleic acid was either photographed or visualized using a fluorimager and the resulting image printed out using a laser printer.

In some cases, size standards were fractionated on the same gel as the target nucleic acid, and used to determine the approximate size of the target nucleic acid. In every case where a gel assay was done, the photograph or fluorimage of the fractionated nucleic acid was inspected for contamination by non-target nucleic acids. For example, images of fractionated samples of plasmid DNA were inspected for RNA, which runs considerably faster than DNA on the same gel, and for chromosomal DNA, which runs considerably slower than plasmid DNA on the same gel. Images of isolated plasmid DNA were also inspected to determine whether most of the plasmid DNA shown in the image is intact, supercoiled plasmid DNA.

Example 2

Absorption Spectrophotometry

Samples of target nucleic acids isolated from various media, as described below, were also analyzed using absorption spectrophotometry. Absorption measurements were taken at wavelengths of 260, 280, and 230 nanometers (nm). $A_{260}/A_{280}$ absorption ratios were computed from the measurements. An $A_{260}/A_{280}$ of greater than or equal to 1.80 was interpreted to indicate the sample analyzed therein was relatively free of protein contamination. The concentration of nucleic acid in each sample was determined from the absorption reading at 260 nm ($A_{260}$).

Example 3

Synthesis of Glycidyl-histidine and Glycidyl-alanine Silica Magnetic Ion Exchange Particles Various two different pH dependent ion exchange ligands, glycidyl-histidine and glycidyl-alanine, were attached to porous silica magnetic particles according to the following procedure. The silica magnetic pH dependent ion exchange particles synthesized as described herein were used to concentrate cells, clear lysates, or isolate target nucleic acids, as described in subsequent Examples, below.

A. Preparation of Glycidyl Modified Silica Magnetic Particles

1. Silica magnetic particles were activated by heating under vacuum at 110° C. overnight.
2. 10 g of the activated particles were suspended in 100 ml of toluene in a flask, and 3.2 ml of 3-glycidylpropyl-trimethoxysilane was added thereto.
3. The flask containing the mixture was fitted with a condenser and the reaction was refluxed for 5 hr. After cooling to room temperature, the reaction mixture sat for 48 hr at room temperature.
4. The reaction mixture was then filtered and the retentate, including glycidyl-modified silica magnetic particles produced in the reflux reaction, were washed with toluene (2×100 ml), hexanes (2×100 ml) and ethyl ether (1×150 ml). The washed product was then left to dry in the air.
5. A small portion of the product was further dried in a 110° C. oven and submitted for elemental analysis. The results (% C 0.75; % H 0.58) are consistent with glycidyl modification of silica gel particles, as illustrated in Formula (I), below. The wavy line in this and other formulae depicted herein and in the remaining Examples below represents the surface of a solid phase, a porous silica magnetic particle in this particular Example.

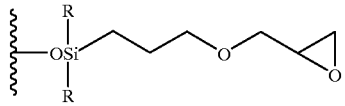
(I)

wherein, R is —OH, OCH$_3$, or —OCH$_2$CH$_3$.

6. The glycidyl-modified silica magnetic particles produced as described above were then further modified by the linkage of an amino acid, such as histidine, alanine, or cysteine to the particles, by reaction with the terminal ring of the glycidyl moiety, as described below.

B. Synthesis of Glycidyl-Histidine Modified Silica Magnetic Particles 1. 2.0 g. of D,L-histidine was dissolved in a mixture of 20 ml of tetrahydrofuran and 20 ml of water by heating the solution to reflux.
2. To this solution, 2 g of glycidyl-modified silica magnetic particles was added and the resulting suspension was refluxed overnight (18 hr).
3. After cooling to room temperature the reaction mixture was filtered, and the retentate, which included glycidyl-histidine modified silica magnetic particles, was washed once with 100 ml of acetone, three times with 150 ml of water, and once with 150 ml of ether. The solid was air dried.
4. A small portion of the dried solid from step 3 was further dried at 110° C. and submitted for elemental analysis. Results: % C 1.35; % H 0.68; % N 0.50. This results are consistent with glycidyl-histidine linkage, such as is as shown in Figure (II), below:

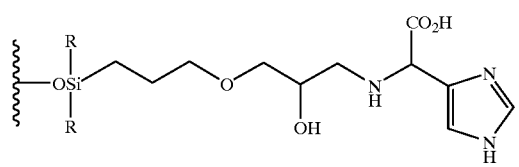
(II)

wherein, R is —H, OCH$_3$, or —OCH$_2$CH$_3$.

C. Synthesis of Glycidyl—Alanine Modified Silica Magnetic Particles 1. 3-(3-pyridyl)-D-alanine (1 g) was dissolved in 20 ml of water.
2. To this solution 2 g. of glycidyl-modified silica magnetic particles were added, and the resulting mixture was refluxed overnight.
3. After cooling, the reaction mixture was filtered and washed twice with water, and once with ethyl ether.
4. Elemental analysis of a sample of the product from step 3 showed: % C 0.98; % H 0.56; % N 0.20. This result is consistent with glycidyl-alanine modification, as illustrated in Formula (III), below:

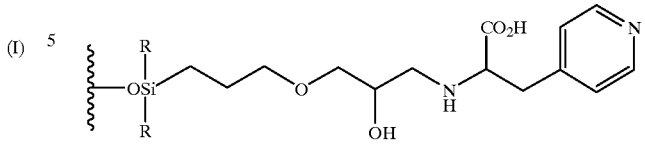
(III)

wherein, R is —OH, OCH$_3$, or —OCH$_2$CH$_3$.

Example 4

Preparation of a Lysate of Plasmid DNA

*E. coli* bacteria cells, DH5α strain, were transformed with pGL3-Control Vector (Promega) plasmid DNA, grown overnight Luria Broth ("LB") medium at 37° C., then harvested by centrifugation.

The following solutions were used to prepare a lysate of the harvested cells, as described below:
Cell Resuspension Solution:
SOmM Tris-HCl, pH 7.5
10 nM EDTA
100 μg/ml DNase-free ribonuclease A (RNase A)
Wizard® Neutralization Buffer (Promega Corp.):
1.32M KOAc (potassium acetate), pH 4.8
Cell Lysis Solution:
0.2M NaOH
1% SDS (sodium dodecyl sulfate)
A lysate of the transformed cells was produced as follows:
1. The cells from 1 to 10 ml of bacteria culture were harvested by centrifuging the culture for 1–2 minutes at top speed in a microcentrifuge. The harvested cells were resuspended in 250 μl of Cell Resuspension Solution, and transferred to a microcentrifuge tube. The resulting solution of resuspended cells was cloudy.
2. 250 μl of Cell Lysis Solution was then added to the solution of resuspended cells and mixed by inversion until the solution became relatively clear, indicating the resuspended cells had lysed.
3. 350 μl of Wizard® Neutralization Buffer was added to the lysate solution, and mixed by inversion. The lysate became cloudy after the Neutralization Solution was added.

Each sample of lysate prepared as described above was cleared, either by centrifugation (control samples), or by using silica magnetic particles or silica magnetic ion exchange particles (test samples), as described in the Examples below.

Example 5

Lysate Clearance by Centrifugation or Silica Magnetic Particles, Followed by Plasmid DNA Isolation Using Glycidyl-histidine or Glycidyl-alanine Silica Magnetic Particles

A. Preparation of Cleared Lysates

Four samples of lysates of 1 ml cultures of DH5α (pGL3) were prepared as described in Example 4, above, except that 24 hour cultures in Circlegrow medium were used instead of overnight LB. Two of the samples were cleared by centrifugation. The other two samples were cleared by mixing the lysate with 150 μl of silica magnetic particles (100 mg/ml), vortexing the resulting mixture until debris in the lysate has adsorbed to the particles, and separating the silica magnetic particles from the solution by magnetic force, using a magnetic separator.

B. Isolation of Plasmid DNA from Cleared Lysates

Plasmid DNA was then isolated from the samples of cleared lysate, as follows:
1. The cleared lysate solutions from both sets of samples were transferred to clean tubes containing 150 μl of either glycidyl-histidine silica magnetic ion exchange particles (hereinafter, "Mag-IE-glycidyl-histidine" particles) or glycidyl-alanine silica magnetic ion exchange particles (hereinafter, "Mag-IE-glycidyl-alanine particles"), and mixed by vortexing. The Mag-IE-glycidyl-alanine and Mag-IE-glycidyl-histidine particles were produced as described in Example 3, above.
2. After waiting 5 minutes for DNA binding to the particles, the solutions were placed on a magnetic rack, allowed to sit for 2 minutes, and the solutions removed.
3. The particles were then resuspended in 1.0 ml of nanopure water, the tubes inverted to wash the side-walls and cap, and placed back into a magnetic separator, which was inverted to wash the tube cap to removed suspended particles.
4. Step 3 (a water wash) was repeated 3 times, for a total of four washes.
5. The solution was removed from the tubes, and the DNA was eluted using (1) 10 mM Tris HCl pH 8.5 for Mag-IE-glycidyl-histidine or (2) 20 mM Tris HCl pH 9.5 for Mag-IE-glycidyl-alanine.

C. Assay of Results

A spectrophotometric assay was conducted on each eluent sample, as described in Example 2. Spectrophotometric results from the Mag-IE-glycidyl-histidine particle eluent showed a yield of 26 μg of DNA and a high purity, with an $A_{260}/A_{280}$ ratio of 1.85. Assay results from the Mag-IE-glycidyl-alanine particle eluent showed a yield of 25 μg of DNA and a $A_{260}/A_{280}$ ratio of 1.90, indicating a comparable purity to the eluent from the other species of IE particle described above.

All the eluents produced as described above were also assayed by gel electrophoresis, as described in Example 1, above. Intact plasmid DNA was detected in each sample, with no evidence of degradation or RNA contamination in any of the samples.

Example 6

Lysate Clearance with Silica Magnetic Particles or Varying Amounts of Mag-IE-glycidyl-histidine Particles The assay described below was performed to determine whether small quantities of silica magnetic ion exchange particles could clear lysate with sufficient efficiency that one could isolate intact plasmid DNA therefrom, which is substantially free of contaminants. Lysate cleared with 4 mg of silica magnetic particles was used as a control. Plasmid DNA was isolated from both the control and test samples of cleared lysate, using Mag-IE-glycidyl-histidine, according to the same procedure, set forth below.

A. Lysate Clearing

Silica magnetic particles and varying amounts of Mag-IE-glycidyl-histidine particles were used, as follows, to prepare a cleared lysate. All the steps below were conducted in 1.5 ml tubes, and at room temperature.

1. A pellet of cells harvested, by centrifugation of a 50 ml overnight culture of DH5α *E. coli* bacteria transformed with pGEM-3Zf+ plasmid DNA, were resuspended in 2.5 ml of Wizard® Resuspension Solution.
2. 265 ®l of the resuspended cells was added to each of eight tubes.
3. 250 μl Wizard™ Lysis solution was added to each tube of resuspended cells, and mixed gently, to avoid possible sheering of genomic DNA.
4. 350 μl Wizard Neutralization solution was added to each tube of lysed cells, and mixed gently and thoroughly.
5. Mag-IE-histidine particles (100 mg/ml) were added to six of the samples from step 4, as follows: 10 μl or 20 μl or 40 μl per lysate tube (in duplicate). 40 μl of silica magnetic particles (100 mg/ml) were added to each of the remaining two samples. All the samples were mixed thoroughly, by vortexing.
6. The resulting particle/cell debris complex was separated from the lysate within each tube, using a magnetic separator. The caps of the tubes were washed four times, by inversion of each tube. The tubes allowed to sit for 1 minute.

B. DNA Isolation

DNA was isolated from each of the cleared lysate samples, above, as described below:
1. Each cleared lysate solution sample, above, was transferred to a clean 1.5 ml tube containing 150 μl of Mag-IE-glycidyl-histidine (10 mg/ml), vortexed, and allowed to sit 5 minutes.
2. The resulting Mag-IE-glycidyl-histidine/DNA complex was then separated from the solution within each tube, using a magnetic separator. The tube caps were each washed four times, by inversion. The tubes were allowed to sit for 1 minute.
3. The liquid was removed from each tube, and discarded.
4. The particles were washed with nanopure water, as follows. 1.0 ml nanopure water was added to each tube, and the particles resuspended therein. The Mag-IE-glycidyl-histidine particles were separated from the solution within each tube, using a magnetic separator. The tube caps were each washed four times, by inversion. The tubes were allowed to sit for 1 minute. The liquid was removed from each tube and cap, and discarded, using the magnetic separator to retain the particles in each tube while the wash solution was discarded.
5. Step 4 was repeated twice, for a total of 3 washes.
6. Added 100 μl 10 mM Tris HCl, pH 8.0, to each tube, and resuspend the particles contained therein by vortexing
7. The plasmid DNA was magnetically separated from the particles from the resulting eluent solution in each tube, and transferred to a clean tube.

C. Assay of Results

Each of the eluent samples produced as described above was assayed spectrophotometrically, as described in Example 2. The assay results are summarized in Table 2, below:

TABLE 1

| PARTICLES & AMOUNT | $A_{260}/A_{280}$ | NUCLEIC ACID YIELD |
|---|---|---|
| 1 mg of Mag-IE-glycidyl-histidine | 1.73 | 37 μg |
|  | 1.73 | 43 μg |
| 2 mg of Mag-IE-glycidyl-histidine | 1.75 | 36 μg |
|  | 1.76 | 38 μg |

TABLE 1-continued

| PARTICLES & AMOUNT | $A_{260}/A_{280}$ | NUCLEIC ACID YIELD |
|---|---|---|
| 4 mg of Mag-IE-glycidyl-histidine | 1.76 | 40 µg |
|  | 1.76 | 38 µg |
| 4 mg of Magnesil ™ | 1.80 | 36 µg |
|  | 1.80 | 37 µg |

The samples assayed by spectrophotometric analysis, as described above, were also analyzed by gel electrophoresis, as described in example 1. FIG. 1 shows a photograph of samples of each of the eluents, above, after being fractionated by gel electrophoresis and stained with ethidium bromide. The samples were loaded on the gel, from left to right, in the same order shown in Table 1, above. None of the samples showed any visible RNA, and the intensity of the plasmid DNA bands is consistent with the yield data obtained by absorption spectrophotometry (as described in example 2).

Example 7

Lysate Clearance by Centrifugation vs. Using Silica Magnetic Particles, Followed by Isolation of Plasmid DNA Form Cleared Lysate Using Silica Magnetic Particles In the following assay, centrifigation or silica magnetic particles were used to clear cell lysates of varying volumes of overnight cultures of the same transformants. Plasmid DNA was then isolated from each cleared lysate solution, using silica magnetic particles, and tested as described below.

A. Lysate Clearing

1. An overnight culture of DH5α(pGL3) was centrifuged to obtain, in six replicates, 1.0 ml, 2.0 ml, and 3 ml cell pellets in 1.5 ml tubes. To each tube, 250 µl of Resuspension Buffer was added, and the cells resuspended by vortexing.
2. 250 µl of Wizard Lysis solution was added per tube, and gently mixed to avoid sheering genomic DNA.
3. 350 µl Wizard Neutralization solution was added per tube, mixed gently and thoroughly.
4. To one set of triplicate samples, the tubes were centrifuged for 10 minutes at 12,000×g to clear the lysate debris. The cleared supernatants were transferred to clean 1.5 ml tubes and processed as described in section B, below.
5. To the other set of triplicate samples (3 of 1.0 ml, 3 of 2 ml, 3 of 3 ml), 50 µl of resuspended silica magnetic particles (100 mgml) were added per lysate tube, and vortexed thoroughly.
6. The resulting particles/cell debris complex was separated from the solution in the tube, in a magnetic separator. Tube caps were washed by tube inversion (4x). Tubes were allowed to sit for 1 minute. The resulting cleared lysate was transferred from the each tube and processed as described in section B, below.

B. Isolation of DNA from Cleared Lysates

1. The cleared solutions from steps 4 and 6, above, were each placed in a clean 1.5 ml tube containing 200 µl of 5.0M guanidine thiocyanate, and vortexed. 150 µl of silica magnetic particles (15 mg) was added per tube, vortexed, and allowed to sit 10 minutes.
2. The resulting silica magnetic particle/DNA complex was separated from the solution in the tube, on a magnetic separator. Tube caps were washed four times, by tube inversion, and allowed to sit in the separator for 1 minute.
3. Liquid was removed from each tube, including caps, and discarded.
4. Each tube was washed with 1 ml of 60 mM KOAc/10 mM Tris-HCl (pH 7.5 at 25° C.)/60% ethanol, using vortexing to resuspend the particles.
5. The silica magnetic particle/DNA complex was separated from the wash solution in the tube, using a magnetic separator. Tube caps were washed four times, by tube inversion, and allowed to sit in the separator for 1 minute.
6. Liquid was removed from tube and caps, and discarded.
7. Steps 4–6 were repeated, for a total of 2 washes.
8. The tubes were allowed to air dry for 30 minutes to remove residual ethanol.
9. 100 µl of nanopure water was added per tube, and the particles were resuspended thoroughly by vortexing. After 10 minutes at ambient temperature, the tubes were placed in a magnetic separator, and the resulting eluent was transferred to clean 1.5 ml tubes.

C. Analysis of Results

The eluent from each sample was analyzed with an absorption spectrophotometer at 230, 260, and 280 nm, as described in Example 3, above. The average value of test results obtained from each set of three samples of eluent, prepared as described above, is set forth in Table 2, below:

TABLE 2

| VOL. CULTURE, CLERANCE MEANS | $A_{230}$ | $A_{260}$ | $A_{280}$ | $A_{260}/A_{280}$ | YIELD (µg DNA) |
|---|---|---|---|---|---|
| 1 ml & Centrifugation | 0.160 | 0.072 | 0.039 | 1.83 | 7.17 |
| 1 ml & Silica Magnetic Particles | 0.176 | 0.094 | 0.053 | 1.77 | 9.36 |
| 2 ml & Centrifugation | 0.197 | 0.121 | 0.667 | 1.82 | 12.0 |
| 2 ml & Silica Magnetic Particles | 0.189 | 0.103 | 0.058 | 1.79 | 10.3 |
| 3 ml & Centrifugation | 0.495 | 0.149 | 0.082 | 1.82 | 14.9 |

The results shown in Table 2, above, indicate comparable amounts of plasmid DNA were isolated from the same volumes of lysate cleared either by centrifugation or by silica magnetic particles. The $A_{230}$ and $A_{260}/A_{280}$ measurements from samples isolated from the same volumes of cultures lysed and cleared with each of the two means described above, indicates that both methods of isolation produced isolated DNA which appears to be free from contamination with low molecular weight alcohol or proteins.

Figure 2:
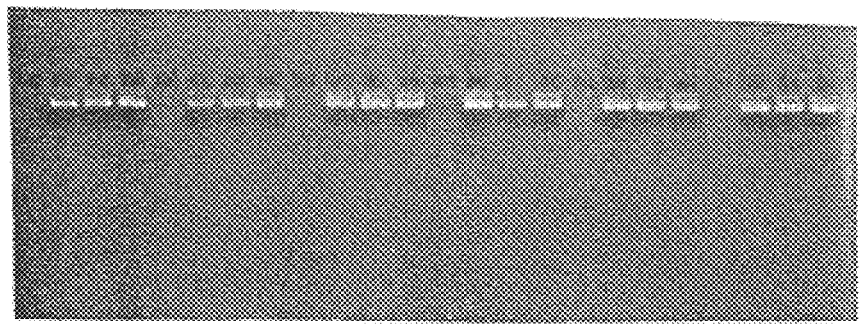
FIG. 2 is a photograph of samples of plasmid DNA isolated from varying amounts of a culture of transformants of E.coli DH5α cells using centrifugation ("Spin") on MagneSil™ particles (Promega Corp.) ("Mag"), followed by fractionation by gel electrophoresis on a short run gel, and visualization by staining with ethidium bromide, as described in Example 7.
Figure 3:
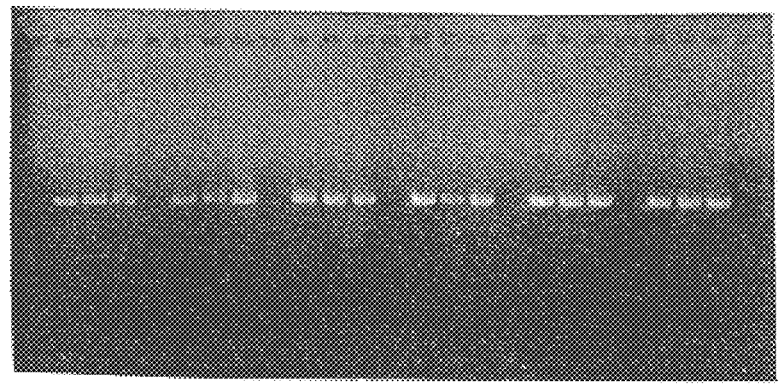
FIG. 3 is a photograph of the same gel shown in FIG. 2, shot after electrophoresis was continued for a longer period of time.

Each of the samples of plasmid DNA isolated as described above was also assayed by agarose gel electrophoresis, as described in Example 1. Initially, the agarose gel with the above samples loaded thereon was run only for a sufficient period of time for the plasmid DNA to migrate into the gel and become separated from any RNA present in each sample. FIG. 2 is a photograph of the gel taken under UV light at this initial stage, after staining the gel with ethidium bromide. No sign of RNA contamination was apparent in any of the lanes of the gel shown in FIG. 2. The same gel was then electrophoresed for an additional period of time, to enable the plasmid DNA to become separated from any chromosomal DNA in each sample loaded thereon. FIG. 3 is a photograph of the same gel, taken under the same conditions described above, after the gel had been run for a longer period of time. No sign of contamination with chromosomal DNA was apparent in any of the lanes of the gel, in FIG. 3.

Example 8

Concentration of Cells, Lysate Clearing, and DNA Isolation Using Mag-IE-glycidyl-histidine Particles Mag-IE-glycidyl-histidine particles were used to concentrate cells prior to lysis, to clear the lysate once the concentrated cells were lysed, and to isolate DNA from the resulting cleared lysate, as follows:

A. Cell Concentration 1. 50 µl of Mag-IE-glycidyl-histidine suspension was aliquoted into each of two 1.5 ml tubes.
2. 500 µl of an overnight culture of DH5α/pGem3Zf+ was aliquoted into the two tubes prepared in step 1. These two samples were processed to harvest the cells as described in steps 4–6, below.
3. 500 µl of the same culture used in step 2 was also aliquoted into each of two empty 1.5 ml centrifuge tubes, and spun in a centrifuge to harvest the cells. The supernatant was discarded, and the harvested cells processed as described in section B, below.
4. 300 µl of SM NaCl was added to each tube of Mag-IE-glycidyl-histidine and overnight culture, and mixed thoroughly.
5. 800 µl of room temperature isopropanol was added to each tube, and mixed thoroughly for a final concentration of 94M NaCl/50% IPA.
6. The resulting Mag-IE-glycidyl-histidine/cells complex was separated from the solution in each tube, in magnetic separator. The solution was discarded, and the harvested cells processed as described in section B, below.

B. Lysate Clearing and DNA Isolation 1. 250 µl Wizard Resuspension solution was added to both sets of tubes, the tubes with cells pelleted in a centrifuge and the tubes with cells complexed with Mag-IE-glycidyl-histidine particles. In both cases, the solutions were mixed thoroughly until the cells were resuspended in each solution.
2. 250 µl of Wizard Lysis solution was added to each tube, and gently mixed to avoid sheering genomic DNA
3. 350 µl of Wizard neutralization solution was added, and mixed gently and thoroughly.
4. The resulting Mag-IE-glycidyl-histidine/cell debris complex was separated from the lysate within each tube, using a magnetic separator.
5. Each resulting cleared lysate solution was transferred to a clean 1.5 ml tube containing 50 µl Mag-IE-glycidyl-histidine, and incubated 2 minutes at room temperature, to enable DNA to adhere to the particles.
6. The resulting Mag-IE-glycidyl-histidine/DNA complex was separated from the solution in the tube, using a magnetic separator.
7. The liquid in the tube was removed and discarded.
8. Each tube was washed with 1.0 ml nanopure water, and the particles suspended therein. The particles were separated from the water in each tube, using a magnetic separator. The liquid was removed and discarded.
9. Step 8 was repeated three times, for a total of four washes.
10. 100 µl of 20 mM Tris pH 9.5, an elution buffer, was then added to each tube. The particles were resuspended in the elution buffer.
11. Magnetic force was used to separated the Mag-IE-glycidyl-histidine particles from the resulting eluent solution.

C. Assay Results

The four samples of DNA isolated from cells which were concentrated by either centrifugation or using Mag-IE-glycidyl-histidine particles, as described above, were assayed spectrophotometrically, as described in Example 1, above. The results of the spectrophotometric analysis are presented in Table 3, below:

TABLE 3

| SAMPLE | $A_{260}/A_{280}$ | YIELD |
| --- | --- | --- |
| Centrifugation used to concentrate cells | 1.84 | 7.8 µg |
|  | 1.85 | 8.1 µg |
| Mag-IE glycidyl-histidine used to concentrated cells | 1.78 | 9.5 µg |
|  | 1.80 | 8.2 µg |

Example 9

Clearing Mouse Tissue Homogenates Using Mag-IE-glycidyl-histidine, and Isolating DNA and RNA therefrom Using Mag-IE-glycidyl-histidine The following protocol was used to clear homogenates of frozen mouse liver, kidney, and spleen tissue, and to isolate RNA and DNA therefrom:

A. Homogenate Clearance

1. A sample of each tissue was homogenized in a solution of 4.5M guanidine thiocyanate (GTC)/132 mM KOAc pH 4.8, wherein, for every 1 mg of tissue, 1 µl of homogenization solution was used. 120 mg of liver, 320 mg of kidney, and 142 mg of spleen were homogenized.
2. The resulting homogenized mixture was diluted 7× with RNase free nanopure water for mouse liver, 6×RNase free nanopure water for Iddney, and 12×RNase free nanopure water for spleen. After the addition of nanopure water (liver=840 µl, spleen=1.7 ml, and kidney=1.9 ml), each sample was vortexed.
3. "½×" volume of Mag-IE-glycidyl-histidine (100 mg/ml) was added to each solution, and vortexed. The resulting mixture was then magnetically separated for 10 minutes.

B. Isolation of Nucleic Acids from Cleared Homogenate

1. An aliquot of each cleared solution separated from the Mag-IE-glycidyl-histidine particles, as described above, was transferred to a clean tube containing Mag-IE-glycidyl-histidine particles. For the liver and spleen samples, 100 µl of cleared solution was added to 100 µl of Magnesil-IE-glycidyl-histidine (100 mg/ml), the mixture was vortexed, allowed to sit for 2 minutes, then allowed to sit in a magnetic separator for 2 minutes. For the kidney sample, 400 µl of cleared solution was added to 1 ml of RNase free nanopure water, then 100 µl of Magnesil-IE-glycidyl-histidine (100 mg/ml) was added, the mixture was vortexed, allowed to sit for 2 minutes, then allowed to sit in a magnetic separator for 2 minutes.
2. The solution was then removed from each tube, and each tube was washed with 1.0 ml RNase free nanopure water, vortexed, and placed back in the magnetic separator. The tube cap was washed by inversion of the tubes in the magnetic rack. After 2 minutes, the wash solution was removed. This wash step was repeated two times, for a total of 3 washes.
3. The nucleic acids were eluted in 100 µl of 10 mM Tris HCl, pH 9.5.

C. Analysis of Results

Figure 4:
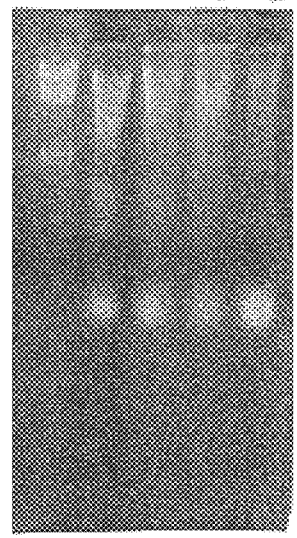
FIG. 4 is a photograph of samples of DNA and RNA isolated from a mouse liver homogenate, using MagIE-glycidyl-histidine particles, as described in Example 9, after fractionation by gel electrophoresis and visualization by staining with ethidium bromide.
Figure 5:
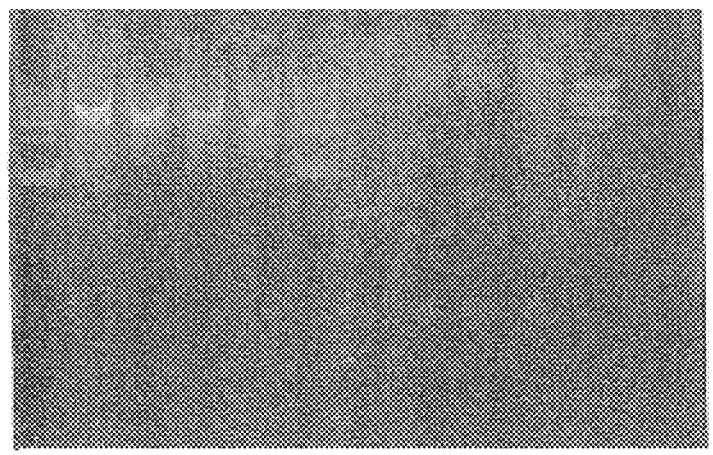
FIG. 5 is a photograph of samples of DNA and RNA isolated from mouse spleen (lanes 2–5) and kidney (lanes 7–9), using MagIE-glycidyl-histidine particles, as described in Example 9, after the samples were fractionated by gel electrophoresis and visualized by staining with ethidium bromide, as described in Example 9.
Figure 6:
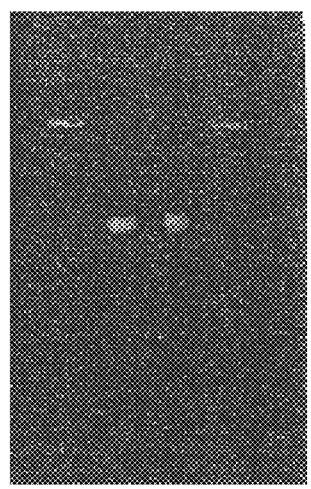
FIG. 6 is a photograph of mouse liver RNA and DNA, after digestion with DNase, fractionation by gel electrophoresis, and visualization by staining with ethidium bromide.

The eluted DNA and RNA was visualized by gel electrophoresis (see example 1) as shown in FIGS. 4, 5, and 6. FIG.

4 shows a photograph of mouse liver DNA and RNA isolated as described above, fractionated by gel electrophoresis along with λ Hind III marker. Both DNA and RNA appear to be present in each eluent.

FIG. 5 shows DNA and RNA isolated from mouse spleen and kidney as described above, after fractionation by gel electrophoresis. Samples were loaded on the gel as follows:

Lane 1: Hind III marker
Lane 2: Spleen, 0 μl removed
Lane 3: Spleen, 20 μl removed
Lane 4: Spleen, 40 μl removed
Lane 5: Spleen, all removed
Lane 6: λ Hind III marker
Lane 7: Kidney, 0 μl removed
Lane 8: Kidney, 20 μl removed
Lane 9: Kidney, all removed
Lane 10: λ Hind III marker FIG. 6 shows samples of mouse liver RNA and DNA isolated as described above, after digestion with DNase and fractionation by gel electrophoresis. Lanes 1 and 4 contain λ Hind III marker, while lanes 2 and 3 contain mouse liver nucleic acid isolated from 200 μl and 400 μl of homogenate, respectively, according to the procedure described above.

Example 10

Concentration of White Blood Cells, Lysate Clearing, and DNA Isolation from Whole Blood Using Mag-IE-gylcidyl-histidine Particles, Non-porous Magnesil-IE-Gly-histidine Particles, and Magnesil™ Particles Using Human Whole Blood Mag-IE-glycidyl-histidine particles, Non-Porous Mag-IE-glycidyl-histidine particles and Magnesil™ particles were used to either (a) concentrate white blood cells, clear the lysate once the concentrated cells were lysed, and to isolate DNA from the resulting cleared lysate, or (b) clear the lysate produced from centrifugal concentrated white blood cells, clear the lysate, and to isolate DNA from the resulting cleared lysate.

A. Use of Mag-IE-glycidyl-histidine Particles with Ion Exchange Wash

Magnetic clearing of blood lysate and purification of genomic DNA using solutions from Promega's Wizard Genomic DNA Purification kit (see, Promega's Technical Manual #TM50), and Mag-IE-glycidyl-histidine particles: All steps were at room temperature. Mag-IE-glycidyl-histidine particles were used with an ion exchange wash to concentrate white blood cells, to clear a lysate of the cells, and to isolate genomic DNA therefrom, as follows:

1. 1.0 ml of blood was placed in a 15 ml tube containing 3.0 ml of Wizard Genomic Cell Lysis solution, mixed, and incubated for 10 minutes.
2. 1.0 ml of 5.0 M NaCl was added, and mixed.
3. 50 μl of Mag-IE-glycidyl-histidine particles in a 100 mg/ml solution was added to the tube, and mixed.
4. 5.0 ml of isopropanol was added and mixed, and incubated for 2 minutes, then placed on a magnetic rack for 5 minutes.
5. The solution was removed and discarded.
6. The tubes were removed from the magnetic rack and vortexed for 5 seconds.
7. 1.0 ml of Nuclei Lysis solution was added, the tube was vortexed for 5 seconds, and incubated for 5 minutes.
8. 330 μl of Wizard Genomic Protein Precipitation solution was added, the tube was vortexed for 5 seconds, and the tube was placed on a magnetic rack for 5 minutes.
9. The cleared lysate solution was removed from the first tube and placed into a second tube containing 200 μl of Mag-IE-glycidyl-histidine particles (100 mglml), and mixed.
10. 0.5 ml of 0.5 M sodium citrate, pH 5.0 (pH adjusted to 5.0 with citric acid) was added, and the solution mixed. 8.0 ml of nanopure water was added, the solution mixed, the tube was incubated for 1 minute, and placed on a magnetic rack for 2 minutes.
11. The solution was removed and discarded.
12. 5.0 ml of 66 mM potassium acetate, pH 4.8 (pH adjusted with acetic acid) was added, the tube vortexed for 5 seconds, and the tube placed on a magnetic rack for 2 minutes.
13. The solution was removed and discarded, and 2.0 ml of 66 mM potassium acetate/600 mM NaCl , pH 4.8 was added, the tube mixed, and placed on a magnetic rack for 2 minutes.
14. The solution was removed and discarded.
15. 2.0 ml of 66 mM potassium acetate, pH 4.8, 450 mM NaCl was added, the tube was vortexed for 5 seconds, and the tube placed on a magnetic rack for 2 minutes.
16. The solution was removed and discarded.
17. 10 ml of nanopure water was added, mixed, and the tube placed onto a magnetic rack for 2 minutes, after which time the solution was discarded.
18. Step 17 was repeated twice, for a total of 3×10 ml nanopure water washes.
19. After removal from the magnetic rack, DNA was eluted in 400 μl of 90 mM Tris HCl, pH 9.5 for 5 minutes. The tube was then placed on a magnetic rack for 5 minutes.

Mag-IE-glycidyl-histidine particles were also used to clear a lysate of white blood cells isolated by centrifugation, before isolating genomic DNA therefrom using the same particles. The same procedure described above was used, except that Steps 2–4 were replaced by centrifugation for 10 minutes at 800×g, followed by removal of the lysed red blood cell debris, and vortexing the cell pellet to resuspend the white blood cells. Also, in step 8, 50 μl of Mag-IE-glycidyl-histidine particles were added after the vortexing step, and followed by five seconds of vortexing, prior to placement of the tube into the magnetic rack.

B. MagneSil™ Particles and Guanidine Thiocyanate

Magnetic clearing of blood lysate and purification of genomic DNA using solutions from Promega's Wizard® Genomic DNA Purification kit, and MagneSil™ particles: guanidine thiocyanate protocol, as described below. All steps were at room temperature 1. 1.0 ml of blood was placed in a 15 ml tube containing 3.0 ml of Wizard Genomic Cell Lysis solution, mixed, and incubated for 10 minutes.
2. 1.0 ml of 5.0 M NaCl was added, and mixed.
3. 50 μl of MagneSil™ Particles, (100 mg/ml) was added to the tube, and mixed.
4. 5.0 ml of isopropanol was added and mixed, and incubated for 2 minutes, then placed on a magnetic rack for 5 minutes.
5. The solution was removed and discarded.
6. The tubes were removed from the magnetic rack and vortexed for 5 seconds.
7. 1.0 ml of Nuclei Lysis solution was added, the tube was vortexed for 5 seconds, and incubated for 5 minutes.

8. 330 µl of Wizard Genomic Protein Precipitation solution was added, the tube was vortexed for 5 seconds, and the tube was placed on a magnetic rack for 5 minutes.
9. 200 µl of MagneSil™ Particles (100 mg/ml) was added to a clean tube, placed on a magnetic rack for 1 minute, and the solution removed. To this tube, the cleared lysate solution was added from the tube in step 8, and mixed.
10. 2.0 ml of 5 M guanidine thiocyanate (GTC) was added, the tube mixed, incubated 2 minutes, and placed on a magnetic rack for 5 minutes.
11. The solution was removed and discarded.
12. 5.0 ml of SV Total RNA Column Wash was added, the tube was vortexed for 5 seconds, and the tube placed on a magnetic rack for 2 minutes.
13. The solution was removed and discarded
14. Steps 12–13 were repeated, for a total of 2 washes.
15. 5.0 ml of 80% ethanol was added, and the tube vortexed for 5 seconds, and the tube placed on a magnetic rack for 2 minutes.
16. The solution was removed and discarded.
17. Steps 15–16 were repeated 2 times, for a total of 3 washes.
18. The tubes were air-dried for 60 minutes in the magnetic rack.
19. After removal from the magnetic rack, DNA was eluted in 400 µl of Wizard Genomic Renaturation Solution for 5 minutes. The tube was then placed on a magnetic rack for 5 minutes.
20. The DNA containing solution was removed to a clean tube.

For the isolation of white blood cells by centrifugation, followed by clearing of the lysate and isolation of DNA with MagneSil™ Particles: Steps 2–4 were replaced by centrifugation for 10 minutes at 800×g, followed by removal of the lysed red blood cell debris, and vortexing the cell pellet to resuspend the white blood cells. Additionally, 50 µl of MagneSil™ particles were added in step 8 after the vortexing step, and followed by five seconds of vortexing, prior to placement of the tube into the magnetic rack.

C. Non-Porous-Mag-IE-glycidyl-histidine Particles and Isopropanol

Magnetic clearing of blood lysate and purification of genomic DNA using solutions from Promega's Wizard Genomic DNA Purification kit, and Non-porous MagneSil-IE-glycidyl-histidine particles, as follows. All steps were at room temperature
1. 1.0 ml of blood was placed in a 15 ml tube containing 3.0 ml of Wizard Genomic Cell Lysis solution, mixed, and incubated for 10 minutes.
2. 1.0 ml of 5.0 M NaCl was added, and mixed.
3. 100 µl of Non-Porous-Mag-IE-glycidyl-histidine in a solution of 100 mg/ml was added to the tube, and mixed.
4. 5.0 ml of isopropanol was added and mixed, and incubated for 2 minutes, then placed on a magnetic rack for 5 minutes.
5. The solution was removed and discarded.
6. The tubes were removed from the magnetic rack and vortexed for 5 seconds.
7. 1.0 ml of Nuclei Lysis solution was added, the tube was vortexed for 5 seconds, and incubated for 5 minutes.
8. 330 µl of Wizard Genomic Protein Precipitation solution was added, the tube was vortexed for 5 seconds, and the tube was placed on a magnetic rack for 5 minutes.
9. The cleared lysate solution was removed from the first tube and placed into a second tube containing 20 mg of Non-Porous-Mag-IE-glycidyl-histidine (200 µl of 100 mg/ml, placed on a magnetic rack and the solution removed), and mixed.
10. 1.0 ml of isopropanol was added, the solution mixed, incubated 2 minutes, then placed in a magnetic rack for 2 minutes.
11. The solution was removed and discarded.
12. 2.0 ml of 66 mM potassium acetate, pH 4.8 (pH adjusted with acetic acid) was added, and the tube vortexed 5 seconds, incubated 1 minute, and the tube placed on a magnetic rack for 2 minutes.
13. The solution was removed and discarded.
14. 2.0 ml of nanopure water was added, mixed, and the tube placed onto a magnetic rack for 2 minutes, after which time the solution was discarded.
15. Step 18 was repeated twice, for a total of 3×2 ml nanopure water washes.
16. After removal from the magnetic rack, DNA was eluted in 400 µl of 90 mM Tris HCl, pH 9.5 for 5 minutes. The tube was then placed on a magnetic rack for 5 minutes.
17. The DNA containing solution was removed to a clean tube.

For the isolation of white blood cells by centrifugation, followed by clearing of the lysate and isolation of DNA with Non Porous-Mag-IE-glycidyl-histidine: Steps 2–4 were replaced by centrifugation for 10 minutes at 800×g, followed by removal of the lysed red blood cell debris, and vortexing the cell pellet to resuspend the white blood cells. Additionally, 100 µl of NP-Mag-IE-glycidyl-histidine particles were added in step 8 after the vortexing step, and followed by five seconds of vortexing, prior to placement of the tube into the magnetic rack.

D. MagneSil-IE-glycidyl-histidine and Isopropanol

The "Non-Porous-Mag-IE-glycidyl-histidine and Isopropanol" method described above was also used with porous Mag-IE-glycidyl-histidine particles. The only changes in the protocol were the use of 50 µl of Mag-IE-glycidyl-histidine instead of 100 µl of Non-Porous-Mag-IE-glycidyl-histidine particles in step 3, and the use of porous Mag-IE-glycidyl-histidine particles in step 8.

For the isolation of white blood cells by centrifugation, followed by clearing of the lysate and isolation of DNA with Mag-IE-glycidyl-histidine particles: Steps 2–4 were replaced by centrifugation for 10 minutes at 800×g, followed by removal of the lysed red blood cell debris, and vortexing the cell pellet to resuspend the white blood cells. Additionally, 50 µl of Mag-IE-glycidyl-histidine particles were added in step 8 after the vortexing step, and followed by five seconds of vortexing, prior to placement of the tube into the magnetic rack.

E. Assay Results

The $A_{260}/A_{280}$ data and DNA yields were calculated from UV spectrophotometry, except for the porous Mag-IE-glycidyl-histidine particles white blood cell concentration samples, where estimates taken from gel electrophoresis were used, as denoted by "(gel)" below. These results are summarized in Table 4, below:

TABLE 4

| PARTICLES USED | METHOD USED | $A_{260}/A_{280}$ | YIELD (µg) |
| --- | --- | --- | --- |
| Porous Mag-IE-glycidyl-histidine | Spin Cells, Clear Lysate (salt wash) | 1.77 1.79 | 11 7 |

TABLE 4-continued

| PARTICLES USED | METHOD USED | $A_{260}/A_{280}$ | YIELD ($\mu$g) |
|---|---|---|---|
| Porous Mag-IE-glycidyl-histidine | Concentrate Cells with Particles, Clear Lysate (salt wash) | 1.27<br>1.29 | 10 (gel)<br>8 (gel) |
| MagneSil ™ | Spin Cells, Clear Lysate (guanidine thiocyanate) | 1.75<br>1.82 | 12<br>10 |
| MagneSil ™ | Concentrate with Particles, Clear Lysate (guanidine thiocyanate) | 1.75<br>1.71 | 8<br>7 |
| Porous Mag-IE-glycidyl-histidine | Spin Cells, Clear Lysate (isopropanol) | 1.76<br>1.78 | 10<br>15 |
| Porous Mag-IE-glycidyl-histidine | Concentrate with Particles, Clear Lysate (isopropanol) | 1.71<br>1.75 | 9<br>13 |
| Non-Porous Mag-IE-glycidyl-histidine | Spin Cells, Clear Lysate (isopropanol) | 1.77<br>1.78 | 4<br>5 |
| Non-Porous Mag-IE-glycidyl-histidine | Concentrate with Particles, Clear Lysate (isopropanol) | 1.65<br>1.57 | 5<br>7 |

We claim:

1. A kit for isolating a target nucleic acid from a disrupted biological material, comprising:
a first container of first magnetic particles with the capacity to form a first complex with a first non-target material in a first solution of disrupted biological material comprising the first non-target material and the target nucleic acid; and
a second container of second magnetic particles with the capacity to form a second complex with the target nucleic acid, under solution conditions designed to promote the specific adsorption of the target nucleic acid to the second magnetic particles.

2. The kit of claim 1, wherein the first magnetic particles, the second magnetic particles, or both the first and second magnetic particles are silica magnetic particles.

3. The kit of claim 1, wherein the first magnetic particles, the second magnetic particles, or both the first and second magnetic particles are pH-dependent ion exchange particles.

4. The kit of claim 1, further comprising a wash solution, configured for use in washing the second complex prior to desorption of the target nucleic acid therefrom.

5. The kit of claim 4, further comprising an elution solution, configured to promote desorption of the target nucleic acid from the second complex.

* * * * *